(12) United States Patent
Ladva et al.

(10) Patent No.: US 10,912,379 B2
(45) Date of Patent: Feb. 9, 2021

(54) ORAL HYGIENE TOOL

(71) Applicants: Suresh Kurji Ladva, Brea, CA (US);
Sonal S Ladva, Brea, CA (US)

(72) Inventors: Suresh Kurji Ladva, Brea, CA (US);
Sonal S Ladva, Brea, CA (US)

( * ) Notice: Subject to any disclaimer, the term of this patent is extended or adjusted under 35 U.S.C. 154(b) by 0 days.

(21) Appl. No.: 16/353,391

(22) Filed: Mar. 14, 2019

(65) Prior Publication Data
US 2020/0288859 A1    Sep. 17, 2020

Related U.S. Application Data

(60) Provisional application No. 62/767,970, filed on Nov. 15, 2018.

(51) Int. Cl.
| *A46B 15/00* | (2006.01) |
| *A46B 9/04* | (2006.01) |
| *A46B 17/08* | (2006.01) |
| *A61B 17/24* | (2006.01) |
| *A47L 13/12* | (2006.01) |

(52) U.S. Cl.
CPC .......... *A46B 15/0081* (2013.01); *A46B 9/04* (2013.01); *A46B 15/0055* (2013.01); *A46B 15/0065* (2013.01); *A46B 15/0095* (2013.01); *A46B 17/08* (2013.01); *A46B 2200/1066* (2013.01); *A47L 13/12* (2013.01); *A61B 17/244* (2013.01)

(58) Field of Classification Search
CPC ....... A46B 9/04; A46B 17/08; A46B 15/0055; A46B 15/0081; A46B 2200/1066; A46B 15/0065; A46B 15/0095; A47L 13/12; A61B 17/244

USPC ...................... 15/111; 211/65, 70.1; 248/110
See application file for complete search history.

(56) References Cited

U.S. PATENT DOCUMENTS

| 1,495,675 A | 5/1924 | Colt |
| 1,728,956 A | 9/1929 | Darmitzel |
| 2,651,068 A | 9/1953 | Seko |
| 4,455,704 A | 6/1984 | Williams |
| 5,980,541 A | 11/1999 | Tenzer |
| D508,325 S | 8/2005 | Zunga |
| D515,817 S | 2/2006 | Siemer |
| D740,941 S | 10/2015 | Ladva |
| 9,232,854 B2 | 1/2016 | Ladva |
| D788,306 S | 5/2017 | Ladva |

(Continued)

*Primary Examiner* — Laura C Guidotti
*Assistant Examiner* — Katina N. Henson
(74) *Attorney, Agent, or Firm* — Eric Karich; Karich & Associates (57) ABSTRACT

A oral hygiene tool has a tongue scraper and a toothbrush. The tongue scraper includes an elongate connector body, a scraper blade being on a first end transverse to the elongate connector body. A slide control mechanism extends from a second end of the elongate connector body. An interlocking structure has a laterally extending ridge. The toothbrush includes an elongate toothbrush body that has a plurality of brushes and a bore that extends into a distal end of the elongate toothbrush body. A slot extends longitudinally along part of the elongate toothbrush body into the bore, while first and second lateral grooves extend laterally into the slot. The interlocking structure is adapted to be slidably inserted into the bore of the elongate toothbrush body such that the interlocking structure is pushed outwardly into the slot of the elongate toothbrush body.

3 Claims, 8 Drawing Sheets

(56) References Cited

U.S. PATENT DOCUMENTS

| | | | |
|---|---|---|---|
| 2003/0034315 A1* | 2/2003 | Tayebi | A47K 1/09 211/65 |
| 2003/0066151 A1* | 4/2003 | Chang | A46B 7/023 15/184 |
| 2009/0235474 A1 | 9/2009 | Seigel | |
| 2015/0007402 A1* | 1/2015 | Ladva | A46B 15/0081 15/111 |

* cited by examiner

ORAL HYGIENE TOOL

CROSS-REFERENCE TO RELATED APPLICATIONS

This application for a utility patent claims the benefit of U.S. Provisional Application No. 62/767,970, filed Nov. 15, 2018.

BACKGROUND OF THE INVENTION

Field of the Invention

This invention relates generally to oral hygiene tools, and more particularly to a tool that includes both a toothbrush and a tongue scraper.

Description of Related Art

Tongue scrapers and toothbrushes are common oral hygiene products. The prior art teaches a simple combination of the two tools; however, the resulting device is unwieldy, and is either too short to use, or too long to store. The present invention addresses those needs by providing a novel and efficient tongue scraper that telescopically engages a toothbrush.

The prior art teaches toothbrushes, tongue scrapers, and the combination of tooth brushes and tongue scrapers. However, the prior art does not teach such a combination with a tongue scraper that telescopically engages a toothbrush, including a locking mechanism for locking the tongue scraper in either a collapsed configuration or an extended configuration. The present invention fulfills these needs and provides further advantages as described in the following summary.

SUMMARY OF THE INVENTION

The present invention teaches certain benefits in construction and use which give rise to the objectives described below.

The present invention provides an oral hygiene tool that includes both a tongue scraper and a toothbrush. The tongue scraper includes an elongate connector body having a first end and a second end; a scraper blade having an elongate upper edge, the scraper blade being positioned on the first end transverse to the elongate connector body; and a slide control mechanism extending from the second end of the elongate connector body, the slide control mechanism having a first prong, a second prong, and an interlocking structure having at least one laterally extending ridge, the interlocking structure being mounted on the second prong. The toothbrush includes an elongate toothbrush body having a proximal end and a distal end; and a plurality of brushes extending from the proximal end of the elongate toothbrush body. A bore extends into the distal end of the elongate toothbrush body, and a slot extends longitudinally along part of the elongate toothbrush body into the bore, while first and second lateral grooves extend laterally into the slot. The interlocking structure is adapted to be slidably inserted into the bore of the elongate toothbrush body such that the first prong biases the second prong outwardly so that the interlocking structure is pushed outwardly into the slot of the elongate toothbrush body, such that the laterally extending ridge is positioned to alternatively engage either the first lateral groove, or the second lateral groove, the lateral groove being positioned to removably lock the tongue scraper in the collapsed configuration, and the second lateral groove being positioned to removably lock the tongue scraper in the extended configuration. The interlocking structure may be pressed inwardly against the bias of the first and second prongs to disengage the laterally extending ridge from either the first or second groove.

A primary objective of the present invention is to provide an oral hygiene tool having advantages not taught by the prior art.

Another objective is to provide an oral hygiene tool having a tongue scraper that slidably engages a toothbrush.

A further objective is to provide an oral hygiene tool with a locking mechanism for locking the tongue scraper in either a collapsed configuration or an extended configuration.

A further objective is to provide an oral hygiene tool that includes a support stand for supporting the oral hygiene tool in an upright position.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above-described drawing figures illustrate the invention, an oral hygiene tool 10 that combines a toothbrush 20 and a tongue scraper 30 that slidably engage each other so that they may be moved between a collapsed and an extended configuration.

Figure 1:
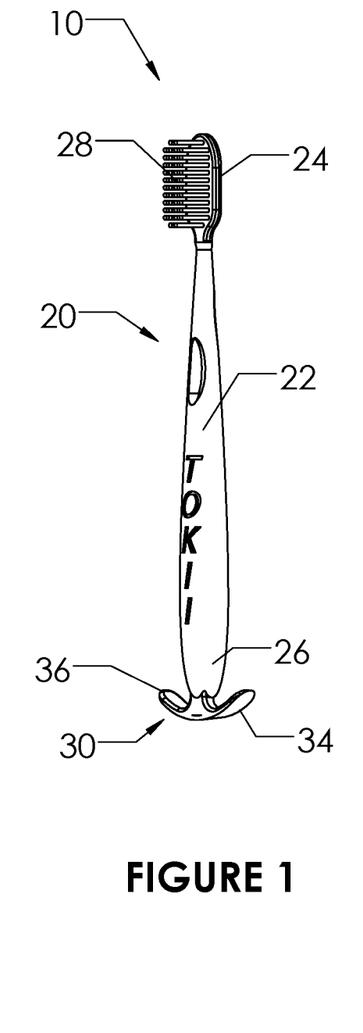
FIG. 1 is a front perspective view of an oral hygiene tool in a collapsed configuration, according to one embodiment of the present invention.

FIG. 1 is a front perspective view of one embodiment of the oral hygiene tool 10, illustrated in the collapsed configuration. As shown in FIG. 1, the toothbrush 20 has an elongate toothbrush body 22 which may be used as a handle for the toothbrush 20, and which telescopically engages the tongue scraper 30. The elongate toothbrush body 22 extends from a proximal end 24 to a distal end 26. A plurality of brushes 28 extend outwardly from the proximal end 24 of the elongate toothbrush body 22 in a configuration suitable for brushing, such as is well known in the art. The brushes 28 may include carbon, charcoal, and/or other materials which facilitate cleaning a person's teeth. The proximal end 24 of the toothbrush body 22 is the end which is inserted into the mouth while brushing. The distal end 26 is the end of the elongate toothbrush body 22 that slidably engages an the tongue scraper 30, as described in greater detail below.

Figure 2:
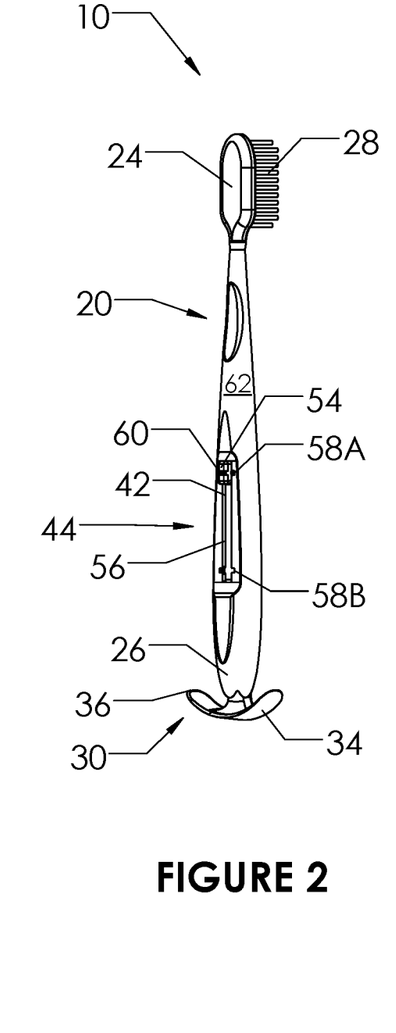
FIG. 2 is a rear perspective view thereof.
Figure 3:
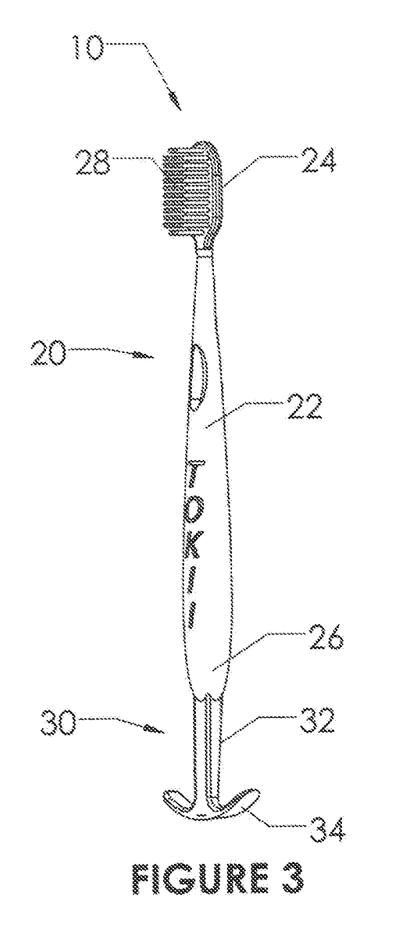
FIG. 3 is a front perspective view of the oral hygiene tool, illustrating the tool in an extended configuration.
Figure 4:
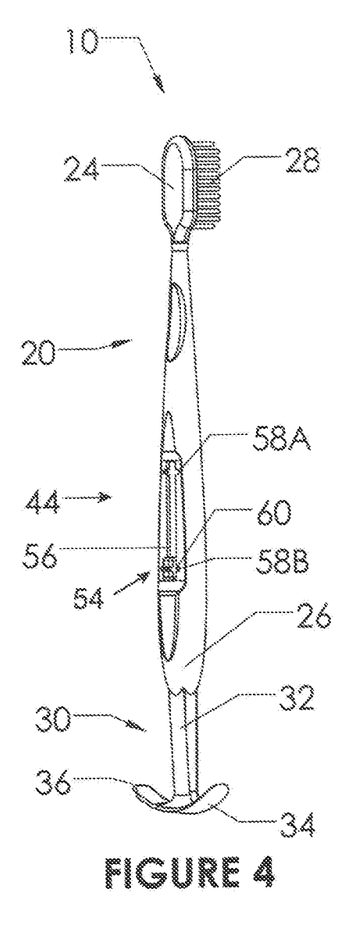
FIG. 4 is a rear perspective view thereof.
Figure 5:
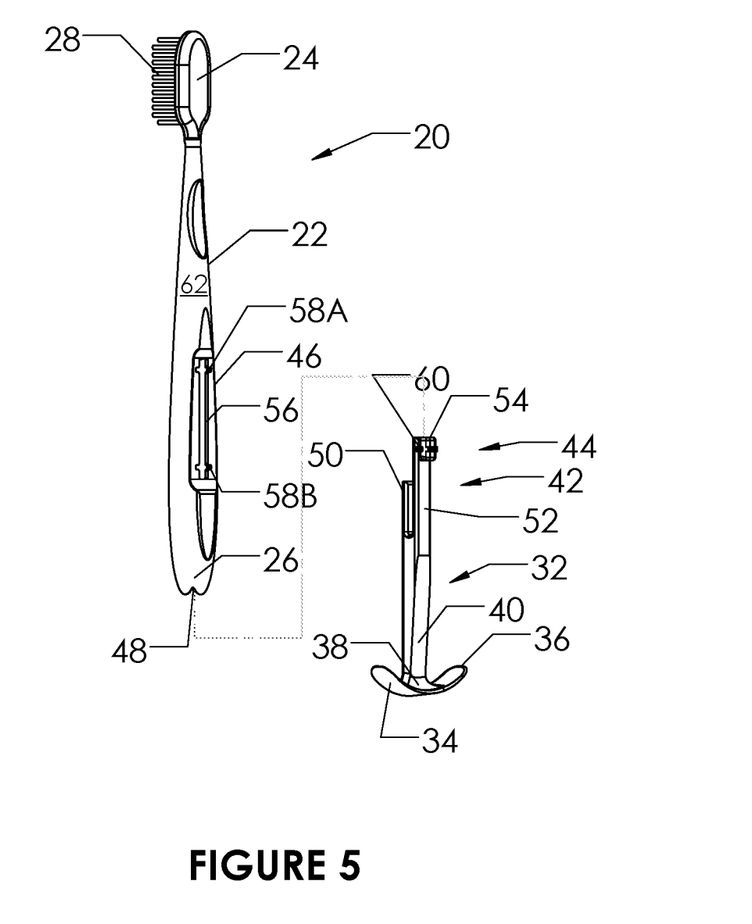
FIG. 5 is an exploded rear perspective view of the oral hygiene tool of FIG. 1.

FIG. 2 is a rear perspective view of the oral hygiene tool 10 of FIG. 1. FIG. 3 is a front perspective view of the oral hygiene tool 10 in an extended configuration. FIG. 4 is a rear perspective view thereof, and FIG. 5 is an exploded rear perspective view thereof. As shown in FIGS. 1-5, the tongue scraper 30 includes an elongate connector body 32 that includes a scraper blade 34. The scraper blade 34 extends laterally on either side of and generally traverses to the elongate connector body 32, and includes an elongate upper edge 36 that is shaped for scraping the tongue. In the present embodiment, the scraper blade 34 is slightly curved and has an upwardly extending wedge-shaped cross section that narrows to the elongate upper edge 36. In other embodiments, the scraper blade 34 may have an alternative structure with any shape known to one skilled in the art for scraping the tongue, and such alternatives should be considered within the scope of the present invention.

As illustrated in FIGS. 1-5, the elongate connector body 32 of the tongue scraper 30 has a first end 40 and a second end 42. The first end 40 is connected with the scraper blade 34, and the second end 42 extends upwardly into the elongate connector body 32 for slidably engaging the toothbrush 20. In the embodiment of FIGS. 1-5, the elongate connector body 32 is a post shaped as an elongate cuboid. In alternate embodiments the elongate connector body 32 may be a structure with any desired shape, e.g. a bar, rod, wedge, or other shape desired by one skilled in the art. In this embodiment, the elongate connector body 32 may also have a sloped front surface 38 where it connects to the scraper blade 34, so as to reduce the obstruction of the portion of the scraper blade 34 that is in contact with the tongue during use, and to eliminate corners/crevices for ease of cleaning. While FIG. 1 illustrates one embodiment of the elongate connector body 32, those skilled in the art may devise alternative embodiments, and these alternatives or equivalents are considered within the scope of the present invention.

Figure 6:
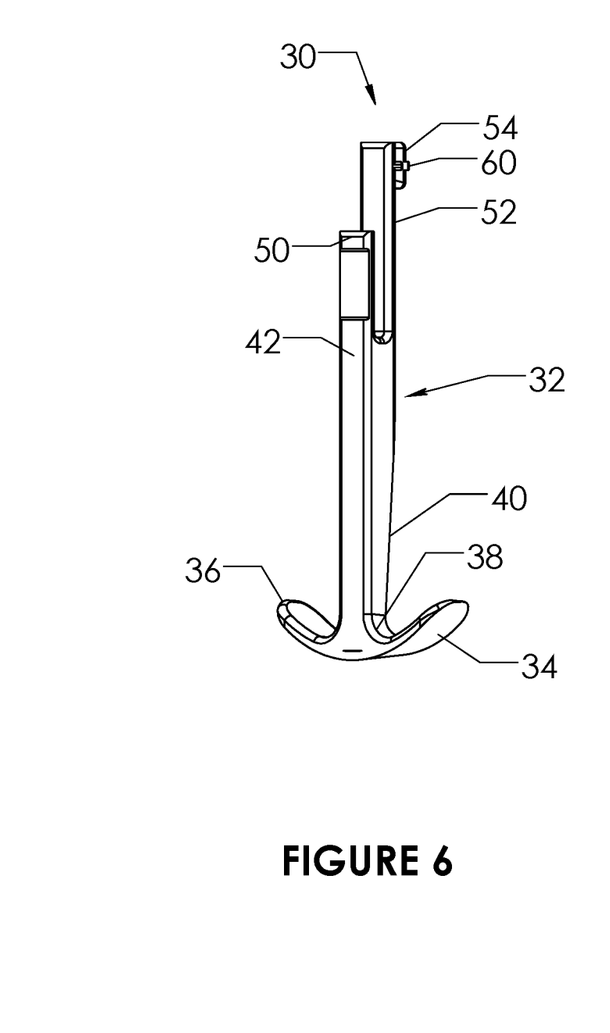
FIG. 6 is a front perspective view of a tongue scraper from the oral hygiene tool of FIG. 1.
Figure 7:
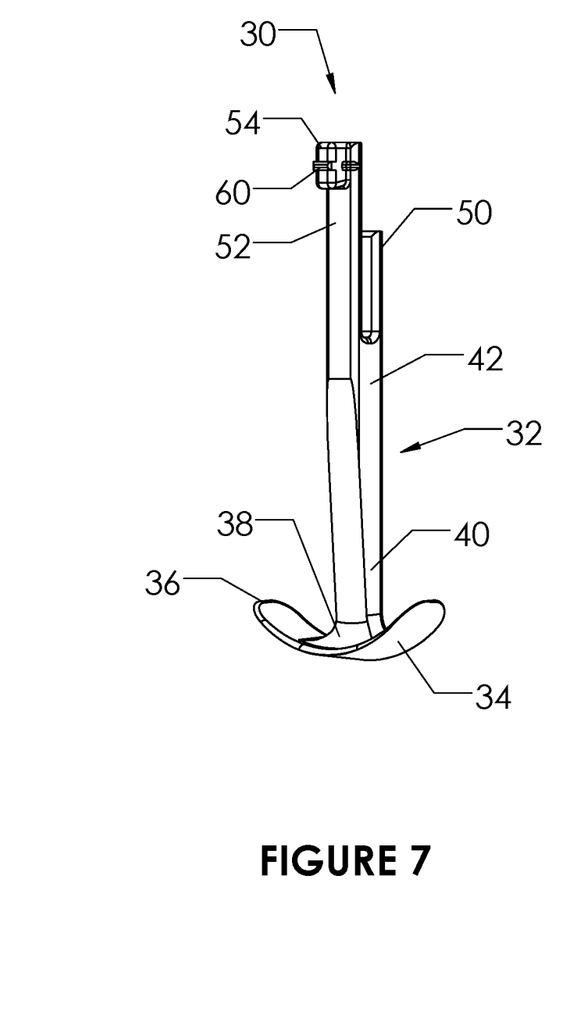
FIG. 7 is a rear perspective view thereof.

FIG. 6 is a front perspective view of the tongue scraper 30 from the oral hygiene tool 10 of FIG. 1. FIG. 7 is a rear perspective view thereof. The second end 42 of the elongate connector body 32, best shown in FIGS. 6-7, includes a slide control mechanism 44 that operatively engages a receiver structure 46 in the toothbrush body 22, best shown in FIGS. 2, 4, and 5. The receiver structure 46 is formed as part of a receiver bore 48 that extends longitudinally into the distal end 26 of the elongate toothbrush body 22, and is approximately the length of the elongate connector body 32. The receiver 46 may have any shape which allows the elongate connector body 32 to telescopically engage with the elongate toothbrush body 22. A square cross-sectional shape, as shown, prevents relative rotation, but in alternative embodiments other cross-sectional shapes may be used.

As shown in FIGS. 6-7, in this embodiment, the slide control mechanism 44 includes a first prong 50 and a second prong 52, both of which are resilient (e.g. molded plastic or other suitable material known in the art). The first prong 50 that is resilient to slide within the bore 48 of the toothbrush body 22, and the second prong 52 is resilient to bias an interlocking structure 54 against the receiver structure 46, which in this embodiment includes a longitudinal slot 56 having first and second lateral grooves 58a & 58b. In this embodiment, the interlocking structure 54 includes a laterally extending ridge 60, so that when the interlocking structure 54 is positioned to extend through the longitudinal slot 56 of the elongate toothbrush body 22, the laterally extending ridge 60 is positioned to alternatively engage either the first or second lateral grooves 58a or 58b that extend into the longitudinal slot 56, the first lateral grooves 58a being associated with the collapsed configuration, and the second lateral grooves 58b being associated with the extended configuration.

In use, the lateral grooves 58a & 58b hold the laterally extending ridge 60 in place, for either storage in the collapsed configuration, or for cleaning the tongue in the extended configuration. When desired, a user may depress the interlocking structure 54 of the slide control mechanism 44 to release it from the lateral grooves 58a or 58b and to slide the elongate connector body 32 to a different configuration.

In alternate embodiments, slide control mechanism 44 may include interlocking bodies, tracks, extensions, or any methods of achieving a telescoping relationship between the tongue scraper 30 and the toothbrush body 22 known by those skilled in the art.

Figure 8:
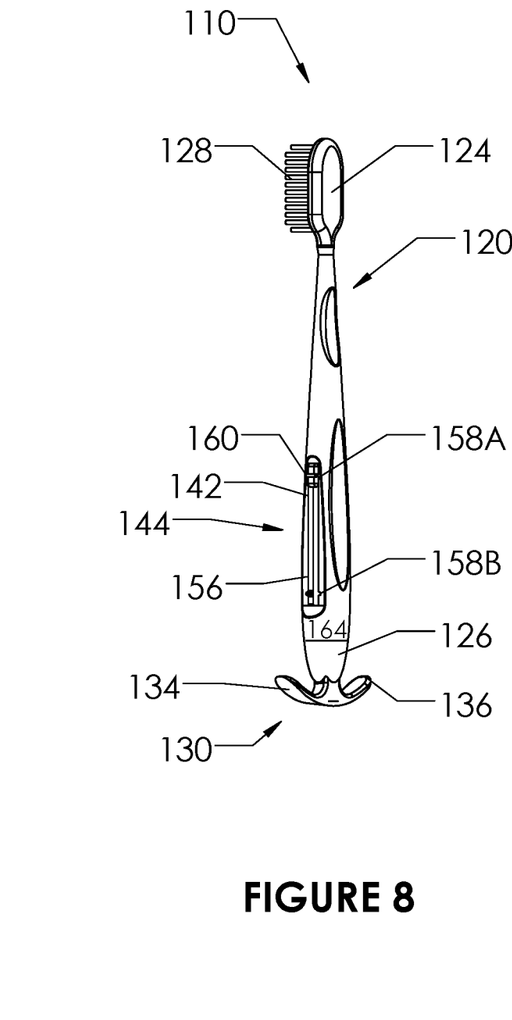
FIG. 8 is a rear perspective view of a second embodiment of the oral hygiene tool, in a collapsed configuration.
Figure 9:
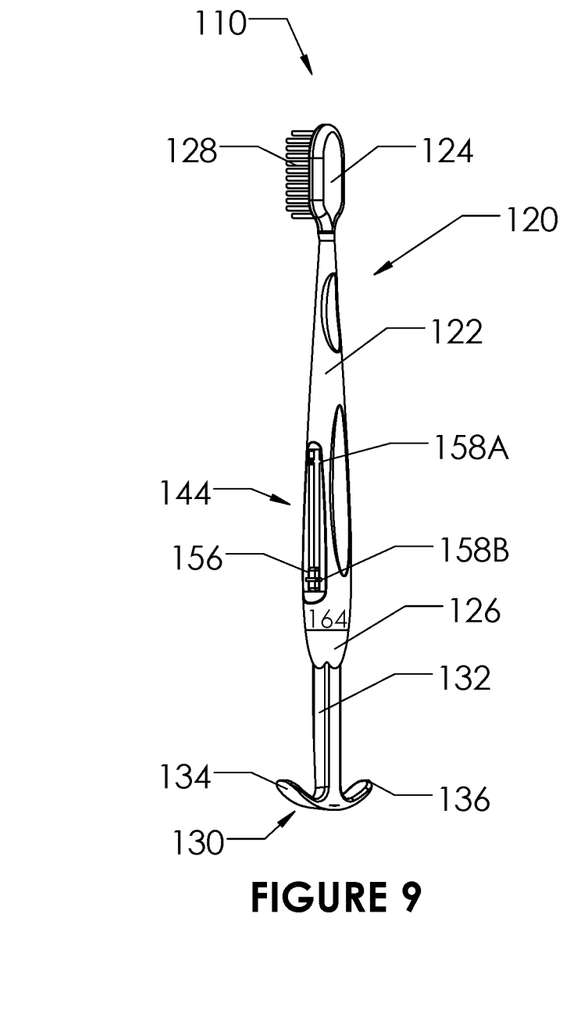
FIG. 9 is a rear perspective view of the oral hygiene tool of FIG. 8, in an extended configuration.
Figure 10:
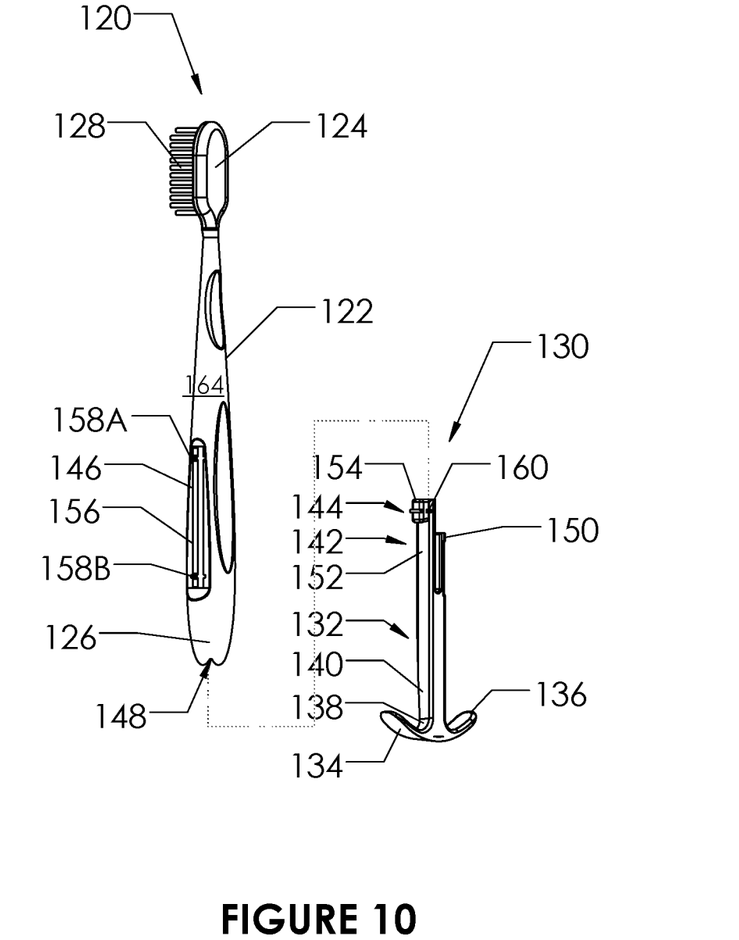
FIG. 10 is an exploded perspective view thereof.

FIG. 8 is a rear perspective view of a second embodiment of the oral hygiene tool 10, in a collapsed configuration. FIG. 9 is a rear perspective view of the oral hygiene tool 10 of FIG. 8, in an extended configuration, and FIG. 10 is an exploded perspective view thereof. In the embodiment of FIGS. 1-7, the longitudinal slot 56 is formed in a rear surface 62 of the elongate toothbrush body 22, but in this embodiment, the longitudinal slot 56 is formed on a side surface 64 of the toothbrush body 22.

As shown in FIGS. 5 and 10, the telescopic construction of the oral hygiene tool 10 may allow for the toothbrush 20 and the tongue scraper 30 to be physically separated, which may be defined as a disengaged configuration. In such a configuration, the toothbrush 20 and/or the tongue scraper 30 may be used separately and/or cleaned, if desired by a user. The act of disengagement is reversible, reassembly possible by inserting the second end 42 of the tongue scraper 30 through the receiver bore 48 of the elongate toothbrush body 22. The ability of the oral hygiene tool 10 to be connected together into a single, compact piece enables the oral hygiene tool 10 to be easily transported and stored.

In one embodiment (not shown), the male/female relationship between the toothbrush 20 and the tongue scraper 30 may be reversed, in which the elongate connector body 32 of the tongue scraper 30 may include an elongate inner chamber (that is similar to the receiving structure of the present embodiment), and the distal end 26 of the toothbrush body 22 telescopically engages the elongate inner chamber.

Figure 11:
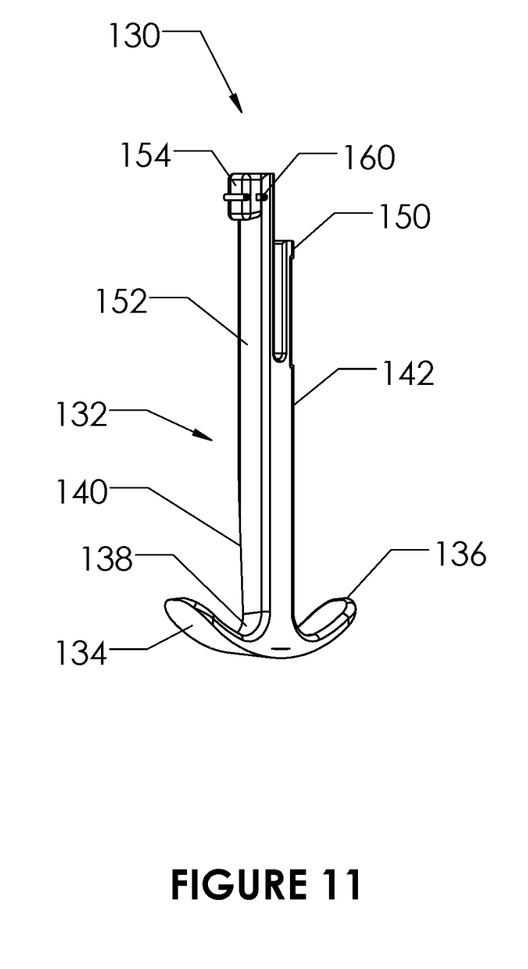
FIG. 11 is a front perspective view of the tongue scraper from the oral hygiene tool of FIG. 8.
Figure 12:
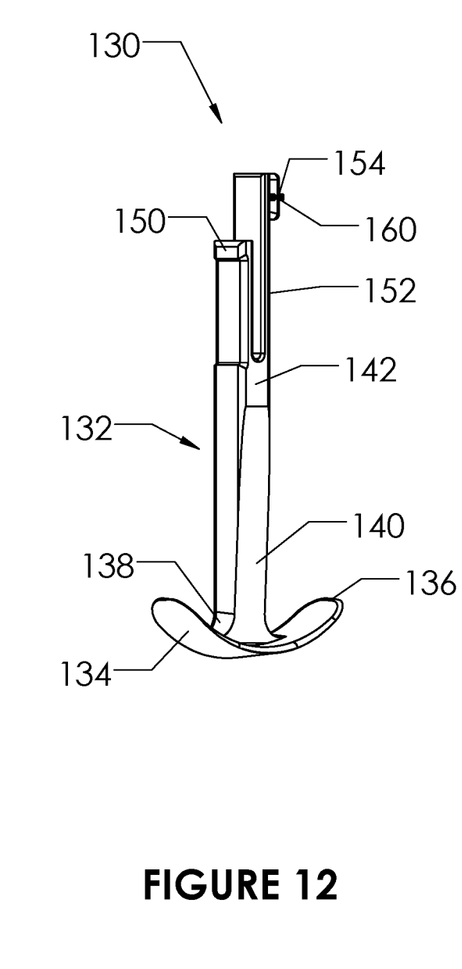
FIG. 12 is a rear perspective view thereof.
Figure 13:
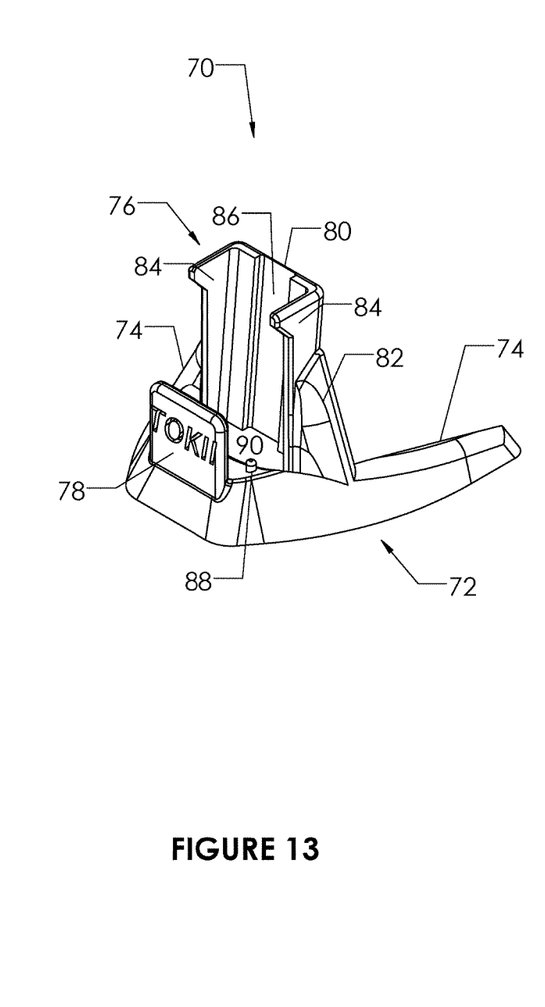
FIG. 13 is a perspective view of a support stand used in conjunction with the oral hygiene tool.
Figure 14:
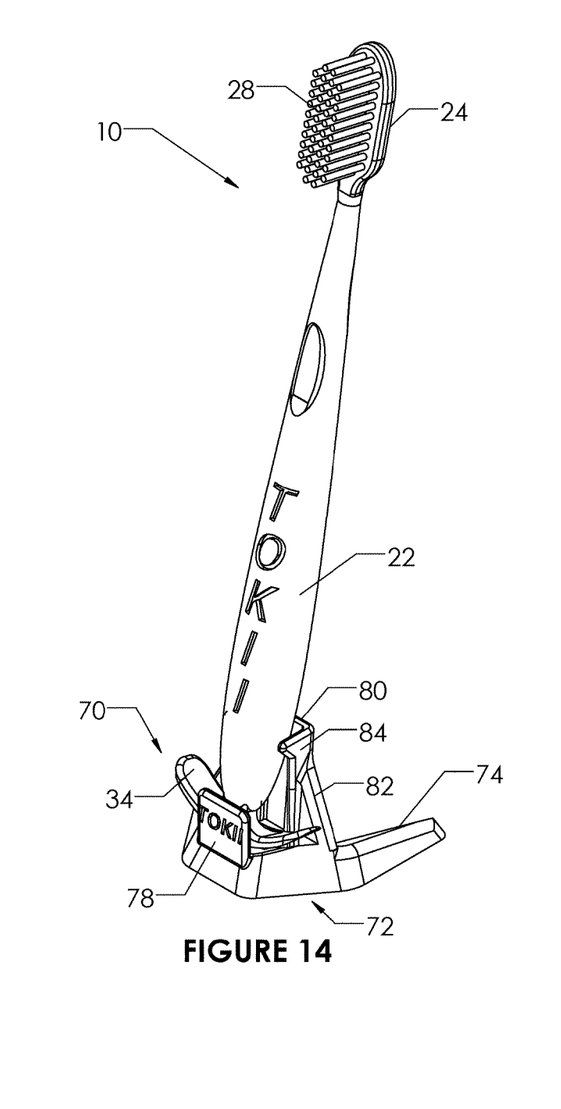
FIG. 14 is a perspective view of the support stand used to support the oral hygiene tool in an upright position.

FIG. 11 is a front perspective view of the tongue scraper 30 from the oral hygiene tool 10 of FIG. 8, and FIG. 12 is a rear perspective view thereof. FIG. 13 is a perspective view of a support stand 70 used in conjunction with the oral hygiene tool 10; and FIG. 14 is a perspective view of the support stand 70 used to support the oral hygiene tool 10 in an upright position. The support stand 70 includes a generally C-shaped base 72 having a horizontal portion in the form of a pair of supporting arms 74 for contact with a flat surface, the base 72 vertically extending into a holding structure 76. The holding structure 76 comprises a front wall 78 extending upwardly from the base 72, and a rear wedge 80, together defining a space shaped to accommodate the oral hygiene tool 10. The rear wedge 80 further comprises side edges 82 that begin at the supporting arms 74 of the base 72, and angle toward each other to meet at vertically extending channel walls 84, the channel walls 84 defining an inner channel 86, so that the oral hygiene tool 10 may be placed in the stand 70 with the elongate toothbrush body 22 resting within the inner channel 86, the scraper blade 34 of the tongue scraper 30 extending laterally between the front wall 78 and the rear wedge 80, and the front wall 78 further securing the elongate toothbrush body 22 in place. Two posts 88 may extend upwardly from the base 72 and within the inner channel 86, so that the scraper blade 34 rests on the posts 88 and is prevented from contacting the base 72 when the oral hygiene tool 10 is placed in the stand 70. The base 72 may further include a gap 90 between the two posts 88 and the inner channel 86, so that any remaining water from use of the oral hygiene tool 10 is hygienically drained and does not stagnate.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. An oral hygiene tool comprising: a tongue scraper comprising: an elongate connector body having a first end and a second end; a scraper blade having an elongate upper edge, the scraper blade being positioned on the first end transverse to the elongate connector body; and a slide control mechanism extending from the second end of the elongate connector body, the slide control mechanism having a first prong, a second prong, and an interlocking structure having at least one laterally extending ridge, the interlocking structure being mounted on the second prong; a toothbrush comprising: an elongate toothbrush body having a proximal end and a distal end; and a plurality of brushes extending from the proximal end of the elongate toothbrush body; a bore extending into the distal end of the elongate toothbrush body; a slot that extends longitudinally through a front surface, a rear surface, or a side surface of the elongate toothbrush body, between the proximal and distal ends, into the bore; and first and second lateral grooves that extend laterally into the slot; wherein the interlocking structure is adapted to be slidably inserted into the bore of the elongate toothbrush body such that the first prong is positioned entirely within the bore and biases the second prong outwardly so that the interlocking structure is pushed outwardly into the slot of the elongate toothbrush body, such that the laterally extending ridge of the second prong is positioned within the slot to alternatively engage either the first lateral groove, or the second lateral groove, the lateral groove being positioned to removably lock the tongue scraper in the collapsed configuration, and the second lateral groove being positioned to removably lock the tongue scraper in the extended configuration; and wherein the interlocking structure may be pressed inwardly against the bias of the first and second prongs to disengage the laterally extending ridge from either the first or second groove.

2. The oral hygiene tool of claim 1, further comprising a support stand comprising:
   a base having a horizontal portion for contact with a flat surface, the base having a pair of supporting arms that extend rearwardly for supporting the base upon the flat surface;
   a front wall extending upwardly from the base opposite the pair of supporting arms, and a rear wedge positioned above the supporting arms, the front wall and the rear wedge being spaced from each other to together define a space shaped to accommodate the oral hygiene tool therebetween;
   wherein side edges of the rear wedge extend upwardly from the pair of supporting arms, and angle toward each other to meet at vertically extending channel walls that define an inner channel of the rear wedge;
   two posts extending upwardly from the base and within the space between the front wall and the rear wedge, so that the scraper blade rests on the posts and is prevented from contacting the base when the oral hygiene tool is placed in the support stand; and
   a gap in the base between the two posts and the rear wedge, so that any remaining water from use of the oral hygiene tool is hygienically drained through the base.

3. The oral hygiene tool of claim 1, wherein the laterally extending ridge includes a pair of laterally extending ridges.

\* \* \* \* \*